United States Patent [19]

Mathur

[11] Patent Number: 5,643,600

[45] Date of Patent: *Jul. 1, 1997

[54] LIPID VESICLES CONTAINING AVOCADO OIL UNSAPONIFIABLES

[75] Inventor: Rajiv Mathur, Sewell, N.J.

[73] Assignee: Micro-Pak, Inc., Wilmington, Del.

[*] Notice: The term of this patent shall not extend beyond the expiration date of Pat. No. 5,260,065.

[21] Appl. No.: 583,667

[22] Filed: Jan. 5, 1996

Related U.S. Application Data

[63] Continuation of Ser. No. 345,223, Nov. 28, 1994, abandoned, which is a continuation of Ser. No. 167,547, Dec. 15, 1993, abandoned, which is a continuation-in-part of Ser. No. 148,952, Nov. 8, 1993, Pat. No. 5,439,967, which is a continuation-in-part of Ser. No. 148,885, Nov. 8, 1993, Pat. No. 5,405,615, each, Continuation-in-part of Ser. No. 761,253, Sep. 17, 1991, Pat. No. 5,260,065.

[51] Int. Cl.$^6$ .............................. A61K 9/127; A61K 7/00
[52] U.S. Cl. ...................... 424/450; 424/401; 428/402.2
[58] Field of Search ........................... 424/450, 401; 428/402; 436/829

[56] References Cited

U.S. PATENT DOCUMENTS

| | | | |
|---|---|---|---|
| 3,069,370 | 12/1962 | Jensen et al. | 260/23 |
| 3,372,201 | 3/1968 | Leary et al. | 260/615 |
| 3,957,971 | 5/1976 | Oleniacz | 424/70 |
| 4,075,131 | 2/1978 | Sterling | 252/542 |
| 4,182,330 | 1/1980 | Michaels | 128/260 |
| 4,235,871 | 11/1980 | Papahadjopoulos et al. | 424/19 |
| 4,241,046 | 12/1980 | Papahadjopoulos | 424/19 |
| 4,247,411 | 1/1981 | Vanlerberghe et al. | 252/316 |
| 4,271,344 | 6/1981 | Vanlerberghe et al. | 424/60 |
| 4,348,329 | 9/1982 | Chapman | 268/483 |
| 4,356,167 | 10/1982 | Kelly | 424/38 |
| 4,377,567 | 3/1983 | Geno | 424/1 |
| 4,399,313 | 8/1983 | Vanlerberghe et al. | 568/622 |
| 4,465,860 | 8/1984 | Vanlerberghe et aql. | 568/36 |
| 4,536,324 | 8/1985 | Fujiwara | 252/311 |
| 4,544,545 | 10/1985 | Ryan et aql. | 424/1.1 |
| 4,551,288 | 11/1985 | Kelly | 264/4.6 |
| 4,610,868 | 9/1986 | Fountain et al. | 424/1.1 |
| 4,666,711 | 5/1987 | Vanlerberghe et al. | 424/70 |
| 4,695,554 | 9/1987 | O'Connell et al. | 436/528 |
| 4,725,442 | 2/1988 | Haynes | 424/490 |
| 4,731,210 | 3/1988 | Weder et al. | 264/4.3 |
| 4,744,989 | 5/1988 | Payne | 424/490 |
| 4,762,915 | 8/1988 | Kung et al. | 530/405 |
| 4,772,471 | 9/1988 | Vanlerberghe et al. | 424/450 |
| 4,789,633 | 12/1988 | Huang et al. | 435/240 |
| 4,830,858 | 5/1989 | Payne et al. | 424/450 |
| 4,832,872 | 5/1989 | Scandel | 252/547 |
| 4,855,090 | 8/1989 | Wallach | 264/4.1 |
| 4,891,208 | 1/1990 | Janoff et al. | 424/1.1 |
| 4,897,308 | 1/1990 | Vanlerberghe et al. | 428/402 |
| 4,911,928 | 3/1990 | Wallach | 424/450 |
| 4,917,941 | 4/1990 | Wallach | 428/402 |
| 5,019,392 | 5/1991 | Wallach | 424/420 |
| 5,021,200 | 6/1991 | Vanlerberghe et al. | 264/4.3 |
| 5,032,445 | 7/1991 | Wallach | 428/402.2 |
| 5,032,457 | 7/1991 | Wallach | 428/402 |
| 5,079,227 | 1/1992 | Jandjani | 514/2 |
| 5,147,723 | 9/1992 | Wallach | 428/402.2 |
| 5,234,767 | 8/1993 | Wallach | 428/402.2 |
| 5,260,065 | 11/1993 | Mathur et al. | 424/450 |

FOREIGN PATENT DOCUMENTS

| | | |
|---|---|---|
| 1539625 | 1/1979 | United Kingdom . |
| 2078543 | 1/1982 | United Kingdom . |
| 2147263 | 5/1985 | United Kingdom . |
| 2166107 | 4/1986 | United Kingdom . |
| 8706499 | 5/1987 | WIPO . |

OTHER PUBLICATIONS

Murahami et al., J. Org. Chem. 47:2137–2144 (1982).
Gregoriadis, N.E. J. Med. 13:704–710 (1976).
Bangham et al. J. Mol. Biol. 13:238–252 (1965).
Szoha et al., Proc. Nat'l. Acad Sci. USA 75:4194–4198 (1978).
Baillie et al., J. Pharm. Pharmacol. 37:863–868 (1985).
Puisieux et al., "Problemes Technologiques Poses Par L'utilisation des Liposomes . . . " (1985) (no translation).
Baille et al., J. Pharm. Pharmacol 38:502–505 (1986).
Dousset et al., "Methods de Preparation des Liposomes . . . " (1985) (no translation).
Ribier et al., Colloids and Surfaces 10:155–161 (1984).
Handjani–Villa, "Les Niosomes" (1985) (no translation).
McCuthcheon, "Detergents and Emulsifiers", No. American Edition (1973).
Gregoriadis, G., Liposome Technology 2nd Ed. vol. 7, Chp. 9 (1993) 141–155.

*Primary Examiner*—Gollamudi S. Kishore
*Attorney, Agent, or Firm*—Lahive & Cockfield, LLP

[57] ABSTRACT

Disclosed are oil-filled paucilamellar lipid vesicles containing at least one non-phospholipid amphiphile as the primary lipid of the vesicle bilayers and avocado oil unsaponifiables. The vesicles are particularly useful for delivering dermatological, cosmetic and pharmaceutical formulations. A method of manufacture for these vesicles is also disclosed.

7 Claims, No Drawings

LIPID VESICLES CONTAINING AVOCADO OIL UNSAPONIFIABLES

REFERENCE TO RELATED APPLICATION

This application is a continuation of application Ser. No. 08/345,223 filed on Nov. 28, 1994 Entitled: LIPID VESICLES CONTAINING AVOCADO OIL UNSAPONIFIABLES now abandoned, which is a continuation-in-part of U.S. patent application Ser. No. 08/148,952, filed on Nov. 8, 1993, now U.S. Pat. No. 5,439,967, and U.S. patent application Ser. No. 08/148,885, filed on Nov. 8, 1993 now U.S. Pat. No. 5,405,615, which are both a continuation-in-part of U.S. Ser. No. 07/761,253, filed on Sep. 17, 1991, now; U.S. Pat. No. 5,260,065.

BACKGROUND OF THE INVENTION

The present invention relates to formulations for lipid vesicles and methods of their manufacture. More particularly, the present invention discloses paucimellar lipid vesicles designed of materials which have exceptional properties for cosmetic, edible, dermatological, and pharmaceutical use. The paucimellar vesicles have 2–10 lipid bilayers surrounding a large, amorphous central cavity which contains a water-immiscible oily material including triglycerides supplied by avocado oil unsaponifiables. The lipid bilayers of these vesicles contain at least one non-phospholipid amphiphile as the primary structural material of the lipid bilayers, along with phytosterol from avocado oil unsaponifiables which acts as a membrane or bilayer modulator.

Lipid vesicles are substantially spherical structures made of amphiphiles, e.g., surfactants or phospholipids. The lipids of these spherical vesicles are generally organized in the form of lipid bilayers, e.g., multiple onion-like shells of lipid bilayers which encompass an aqueous volume between the bilayers. Paucilamellar lipid vesicles have 2–10 peripheral bilayers which surround a large, unstructured central cavity.

Until recently, liposome technology has been concerned mostly with vesicles composed of phospholipids. This is primarily because phospholipids are the principal structural components of natural membranes and, accordingly, lipid vesicles have been used as a model system for studying natural membranes. However, there are a number of problems associated with using phospholipids as synthetic membranes. Biological membranes are stabilized by membrane proteins and maintained by extensive enzymatic "support" systems that rapidly turn over, exchange or modify membrane lipids. Neither membrane proteins nor the requisite enzymatic support systems can be practically incorporated into the wall structure of liposomes, making the structures inherently less stable than natural membranes. In addition, the biological environment contains several potent phospholipases that rapidly break down free phospholipids. These phospholipids will attack liposomes and degrade the membrane. For these reasons, phospholipid liposomes placed in an in vivo environment are rapidly degraded.

Moreover, phospholipid liposome technology has other problems. Phospholipids are labile and expensive to purify or synthesize. In addition, classic phospholipid liposomes are in the form of multilamellar as opposed to paucilamellar vesicles and have poor carrying capacities, especially for lipophilic materials, and have poor shelf lives unless lyophilized in the dark with antioxidants. While unilamellar vesicles (these only having one bilayer) add additional carrying capacity, they are much less stable. Finally, phospholipids degrade too rapidly in vivo for most pharmaceutical or vaccine applications.

For these reasons, there is increasing interest in liposomes made of commercially available nonphospholipid amphiphiles (see, e.g., U.S. Pat. No. 4,217,344, U.S. Pat. No. 4,917,951, and U.S. Pat. No. 4,911,928). These molecules have a hydrophilic "head" group attached to a hydrophobic "tail" and are derived from long chain fatty acids, long chain alcohols and their derivatives, long chain amines, and polyol sphingo- and glycerolipids. Commercially available amphiphile surfactants include, for example, the BRIJ family of polyoxyethylene fatty ethers, the SPAN sorbitan fatty acid esters, the TWEEN ethoxylated sorbitan fatty acid esters, glyceryl monostearate, glyceryl distearate, and glyceryl dilaurate, all available from ICI Americas, Inc. of Wilmington, Del.

Paucilamellar vesicles comprised of such non-phospholipid amphiphiles provide a number of advantages over classical phospholipid multilamellar liposomes. For instance, these vesicles have a high carrying capacity for water-soluble and water immiscible substances. Also, the amphiphiles used to make up the vesicle bilayers can often be used as emulsifiers or thickeners, providing the "feel" to certain cosmetics and/or dermatologicals. Furthermore, many of these amphiphiles fall under the GRAS list of edible materials and therefore can be used in many food and pharmaceutical products.

It has previously been shown that when forming lipid vesicles containing at least one amphiphile as the primary lipid of the bilayers, the addition of a membrane modulator considerably improves the shape and size of lipid vesicles, as well as the consistency of the formulation after processing (See e.g., U.S. Pat. No. 5,260,065). In the past, cholesterol has generally been used for this purpose. Sterols such as cholesterol also act to modify the thermotropic phase transition of the amphiphiles. However, cholesterol has the drawback of being an undesirable ingredient for use in most edible and pharmaceutical preparations.

Avocado oil unsaponifiables (a source of phytosterol) can be used instead of cholesterol as a bilayer modulator and provides many cosmetic, dermatological and pharmaceutical benefits. For example, it has a soft waxy consistency that confers a creamy texture to skin care products in addition to its moisturizing effects. Avocado oil unsaponifiables are also non-cytoxic, non-irritating and edible.

Accordingly, an object of the present invention is to provide a method of making paucimellar lipid vesicles using materials which are edible and/or have cosmetic, dermatological and pharmaceutical benefits.

Another object of the invention is to provide paucilamellar lipid vesicles which contain a blend of at least one non-phospholipid amphiphile as the primary structural material of the bilayers and phytosterol supplied by avocado oil unsaponifiables as a modulator.

A further object of the invention is to provide a method of producing paucimellar lipid vesicles which readily encapsulate water immiscible oily materials and are manufactured from relatively inexpensive materials.

These and other objects and features of the invention will be apparent from the following description and the claims.

SUMMARY OF THE INVENTION

The present invention features paucilamellar lipid vesicles having 2–10 bilayers surrounding an amorphous central cavity which is substantially filled with an oily material. The lipid bilayers contain at least one non-phospholipid amphiphile as the primary lipid and phytosterol supplied by avocado oil unsaponifiables as a modulator. The lipid bilayers may further contain a negative charge producing agent, such as dicetyl phosphate, oleic acid, stearic acid, or mixtures thereof or a positive charge producing agent, such as quaternary ammonium compounds. The term "primary lipid", as used herein, means that this lipid is the major lipid, by weight, forming the structure of the lipid bilayers.

In a preferred embodiment, the primary non-phospholipid amphiphile is selected from the group consisting of polyoxyethylene fatty esters, polyoxyethylene fatty acid ethers, diethanolamides, long chain acyl hexosamides, long chain acyl amino acid amides, long chain acyl amides, polyoxyethylene derivatives of fatty acid esters having 10–20 oxyethylene groups, polyoxyethylene 20 sorbitan mono- or trioletate, polyoxyethylene glyceryl monostearate with 1–10 oxyethylene groups, and glycerol monostearate. In another preferred embodiment, the bilayers further contain a phospholipid, a glycolipid, and mixtures thereof In yet another preferred embodiment, the primary non-phospholipid amphiphile is selected from the group consisting of betaines and anionic sarcosinamides.

In still another preferred embodiment, the bilayers contain both a primary non-phospholipid amphiphile selected from the group consisting of $C_{12}$–$C_{18}$ fatty alcohols, $C_{12}$–$C_{18}$ glycol monoesters, $C_{12}$–$C_{18}$ glyceryl mono- and diesters, propylene glycol stearate, sucrose distearate, and mixtures thereof; and a second non-phospholipid amphiphile selected from the group consisting of quaternary dimethyldiacyl amines, polyoxyethylene acyl alcohols, polyglycerols, sorbitan fatty acid esters, polyoxyethylene derivatives of sorbitan fatty acid esters, fatty acids and their salts, and mixtures thereof.

The present invention further relates to a method of forming the paucilamellar lipid vesicles of the invention. A lipophilic phase containing at least one non-phospholipid amphiphile is first prepared and then blended with avocado oil unsaponifiables and any other oily material to be encapsulated into the vesicle to form a lipid phase. This lipid phase is then shear mixed with an aqueous phase containing an aqueous-based hydrating agent and any aqueous soluble material to be encapsulated into the vesicle to form lipid vesicles. "Shear mixing" is defined as the mixing of the lipid phase with the aqueous phase under turbulent or shear conditions which provide adequate mixing to hydrate the lipid and form lipid vesicles. "Shear mixing" is achieved by liquid shear which is substantially equivalent to a relative flow rate for the combined phase of about 5–30 m/s through a 1 mm orifice.

In order to achieve the proper blending necessary to form the paucilamellar vesicles of the present invention, all of the materials are normally in flowable state. This is easily achieved by elevating the temperature of the lipid phase in order to make it flowable followed by carrying out the shear mixing between the lipid phase and the aqueous phase at a temperature such that both phases are liquids.

All of the materials used to form the vesicles of the invention can also be used in the methods of the invention. Other modifications of the methods and products will be apparent from the following description and claims.

DETAILED DESCRIPTION OF THE INVENTION

The lipid vesicles of the invention are paucilamellar lipid vesicles characterized by two to ten lipid bilayers or shells with small aqueous volumes separating each substantially spherical lipid shell. The innermost lipid bilayer surrounds a large, amorphous central cavity which is substantially filled with an oily solution.

The lipid bilayers of the vesicles contain a blend of at least one non-phospholipid amphiphile as the primary lipid of the bilayers and phytosterol supplied by avocado oil unsaponifiables which acts as a modulator. The avocado oil unsaponifiables provides two distinct benefits: first, it acts as a source of phytosterol for the bilayers, and second, it acts as a source of triglycerides which substantially fill the amorphous central cavity of the vesicles and serve as a moisturizer. This oily material also acts as a vesicle stabilizer. The central cavity may further contain other oily materials.

The following Examples will clearly illustrate the efficacy of the invention.

EXAMPLE 1

In this Example, oil-filled lipid vesicles were formed using avocado oil unsaponifiables obtained from Croda Inc., Parsippany N.J., with and without additional cholesterol, as a component of the lipid bilayers. Propylene glycol stearate was used as the primary amphiphile of the lipid bilayers. Polysorbate 60 (polyoxyethylene 20 sorbitan monostearate) and/or stearyl alcohol were added to Samples A, C and D as secondary amphiphiles or spacers.

TABLE 1

| | Sample | | | |
|---|---|---|---|---|
| Composition (grams) | A | B | C | D |
| Propylene Glycol Stearate | 1.75 | 2.5 | 2.5 | 2.5 |
| Stearyl Alcohol | 0.35 | | 0.5 | 0.5 |
| Polysorbate 60 | 0.25 | | | 0.35 |
| Cholesterol | | | | 0.5 |
| Avocado Oil Unsaponifiables* | 4.0 | 2.5 | 2.5 | 2.5 |
| Water | 28.6 | 30 | 30 | 29 |

*1 gram Avocado oil unsaponifiables contains about 0.3 grams phytosterol

In this Example, oil-filled vesicles were formed using the hot loading technique described in U.S. Pat. No. 4,911,928, the disclosure of which is incorporated herein by reference. Briefly, the vesicles were hot loaded by heating the lipid phase consisting of avocado oil unsaponifiables and the appropriate amphiphile(s) to 85° C., and then hydrating the lipid phase by the aqueous phase at 65° C.

Hydration to form lipid vesicles was achieved by shear mixing the lipid and aqueous phases using two 60 cc syringes, connected by a stopcock. The lipid and aqueous phases were blended from one syringe to the other, forming vesicles in two minutes or less. However, in this and the following Examples, any method of achieving the proper shear could be used. Preferably, a flow device such as the NovaMix™ vesicle former is used. The basic details of the NovaMix™ system are described in U.S. Pat. No. 4,895, 452, the disclosure of which is incorporated herein by reference.

After processing to form lipid vesicles, sample B had a cottage cheese-like consistency, while sample C had only partially hydrated lipid and clear water. These samples were not examined further.

After processing to form lipid vesicles, samples A and D had a smooth, lotion-like consistency. Microscopic examination of these samples showed nice, small, spherical vesicles with maltese crosses, indicating multiples concentric lipid bilayers. The mean diameters of these vesicles measured 1460 nm and 913 nm respectively. When centrifuged at 3500 rpm for 30 minutes, samples A and D both showed some separation, probably due to an excess of water. Sample A, which contained 4.0 grams of avocado oil unsaponifiables with no additional cholesterol, contained a slightly better, more homogenous population of vesicles than did sample D, which contained cholesterol and only 2.5 grams of avocado oil unsaponifiables.

This Example shows that avocado oil unsaponifiables, preferably ranging from 20–65 percent by weight of the lipid, can be used along with or, more preferably, instead of cholesterol in the formation of oil-filled lipid vesicles. Avocado oil unsaponifiables provides the advantage of acting both as a source of phytosterol in the lipid bilayers, as well as a source of triglycerides which partially fill the central cavity of the vesicles, serving as a moisturizing agent

EXAMPLE 2

In this Example, samples A–C were designed to form oil-filled paucilamellar vesicles using as the primary structural components of the lipid bilayers an amphiphile selected from the group consisting of glyceryl dilaurate, glyceryl monostearate, or glyceryl distearate, and phytosterol from avocado oil unsaponifiables (obtained from Croda Inc., Parsippany, N.J.). Samples B and C also contained a secondary amphiphile which acted as a spacer molecule, consisting of either Polysorbate 60 (polyoxyethylene 20 sorbitan monostearate) or Brij 76 (polyoxyethylene 10 stearyl alcohol).

TABLE 2

| Vesicle Components (grams) | A | B | C |
| --- | --- | --- | --- |
| Brij 76 | | | 1.6 |
| Glyceryl Dilaurate | 3.0 | | |
| Glyceryl Monostearate | | 2.55 | |
| Glyceryl Distearate | | | 2.0 |
| Polysorbate 60 | | 0.67 | |
| Avocado Oil Unsaponifiables* | 3.0 | 4.0 | 4.0 |
| Water | 30.0 | 35.0 | 40.0 |

*1 gram of Avocado Oil Unsaponifiables contains approximately 0.3 grams of phytosterol.

Oil-filled vesicles were formed using the hot loading technique described in Example 1, except that the aqueous phase was heated to 70° C. instead of 65° C.

After processing to form lipid vesicles, all three Samples had a nice fluid consistency. Upon microscopic examination, Sample A had two populations of vesicles consisting of small, birefringent vesicles with maltese cross patterns (indicating multiple concentric bilayers) and larger, aggregated vesicles. Sample B contained small, hetro-sized, birefringent vesicles with maltese cross patterns. Sample C contained the best vesicles of the three samples and was made up of homogenous, small, birefringent vesicles with maltese cross patterns. The mean particle diameter of the vesicles of Samples A–C, measured by Coulter Counter (Coulter Counter Electronics Corp., Miami, Fla.), was approximately 1190 nm, 1420 nm and 380 nm, respectively.

After centrifugation at 3500 rpm for 15 minutes, Sample A (containing no secondary amphiphile) separated into two phases consisting of approximately 25 ml of turbid solution at the bottom of the Sample and approximately 10 ml of creamy solution at the top. Samples B and D showed no separation, probably due to the addition of a secondary amphiphile.

These results show that paucilamellar lipid vesicles can be formed using avocado oil unsaponifiables instead of cholesterol or other membrane modulators, along with an amphiphile, to form the lipid bilayers of paucilamellar vesicles. The addition of a secondary amphiphile, preferably Brij 76 (See Sample C), improves the size and shape of the vesicles. Avocado oil unsaponifiables provides the advantage of acting both as a source of phytosterol in the lipid bilayers, as well as a source of triglycerides which are encapsulated in the central cavity and serve as a moisturizing agent.

EXAMPLE 3

In this Example, oil-filled paucilamellar lipid vesicles were formed using avocado oil unsaponifiables (obtained from Croda Inc., Parsippany, N.J.) along with a primary amphiphile consisting of either polyoxyethylene 2 cetyl ether (Brij 52) or polyoxyethylene 9 glyceryl monostearate (POE 9 GMS). For Samples B and C, phosphate buffer saline (PBS) was used instead of water as the hydrating agent.

TABLE 3

| | Sample | | | |
| --- | --- | --- | --- | --- |
| Vesicle Components (grams) | A | B | C | D |
| Brij 52 | 1.8 | 1.8 | | |
| POE 9 GMS | | | 2.7 | 2.7 |
| Avocado Oil Unsaponifiables* | 1.2 | 1.2 | 1.7 | 1.7 |
| Water | 16.0 | | 13.0 | |
| PBS | | 16.0 | | 13.0 |

*1 gram of Avocado Oil Unsaponifiables contains approximately 0.3 gm of phytosterol.

Oil-filled vesicles were formed using the hot loading technique described in Example 1, except that the lipid phase was heated to 70° C. and hydrated by the aqueous phase at 65° C. Hydration to form lipid vesicles was achieved using 20 cc syringes in place of the 60 cc syringes used in Example 1.

After processing for lipid vesicles, Samples A and B were thick and viscous, while Samples C and D were fluid.

Microscopic examination of all four samples showed very nice, small, spherical vesicles. The mean particle diameter of the vesicles of Samples A–D were 1040 nm, 809 nm, 444 nm and 430 nm, respectively.

This Example shows that the combination of POE 9 GMS and avocado oil unsaponifiables forms better vesicles, both in shape and in consistency of formulation, than does the combination of Brij52 and avocado unsaponifiables. This Example also shows that PBS can be used instead of water as a hydrating agent.

EXAMPLE 4

In this Example, a variety of different primary amphiphiles were used in combination with avocado oil unsaponifiables (obtained from Croda Inc., Parsippany, N.J.) to form the lipid bilayers of oil-filled paucilamellar vesicles. For each Sample, vesicles were made with phytosterol, supplied by avocado oil unsaponifiables, being 15% by weight of bilayer material and 3.8% by weight of the total vesicle.

TABLE 4

| | | Avacado Oil Unsaponifiables* | Water | |
|---|---|---|---|---|
| A | POE10 Cetyl Alcohol (Brij 56) | 1.7 gm | 1.0 gm | 16 ml |
| B | POE2 Stearyl Alcohol (Brij 72) | 1.7 gm | 1.0 gm | 16 ml |
| C | POE10 Stearyl Alcohol (Brij 76) | 1.7 gm | 1.0 gm | 16 ml |
| D | POE10 Oleyl Alcohol (Brij 97) | 1.7 gm | 1.0 gm | 16 ml |
| E | POE4 Lauryl Alcohol (Brij 30) | 1.7 gm | 1.0 gm | 16 ml |
| F | POE2 Oleyl Alcohol (Brij 92) | 1.7 gm | 1.0 gm | 16 ml |
| G | POE20 Sorbitan Monostearate (Tween 60) | 1.7 gm | 1.0 gm | 16 ml |
| H | POE20 Sorbitan Monooleate (Tween 80) | 1.7 gm | 1.0 gm | 16 ml |
| I | POE8 Stearate (Myrj 45) | 1.7 gm | 1.0 gm | 16 ml |
| J | DEA Lactic Amide (Mona 150 LWA) | 1.7 gm | 1.0 gm | 16 ml |
| K | DEA Lauric Amide (Mona 150 LWA) | 1.7 gm | 1.0 gm | 16 ml |
| L | DEA Linoleic Amide (Mona 15–70w) | 1.7 mg | 1.0 gm | 16 ml |

*1 gram of Avocado Oil Unsaponifiables contains approximately 0.3 gm of phytosterol
*POE is polyoxyethylene
*DEA is diethanolamide Oil-filled vesicles were formed using the hot loading method described in Example 1, except that the lipid phase was heated to 7020 C. and hydrated by the aqueous phase at 60° C. Hydration to form lipid vesicles was achieved using 20 cc syringes in place of the 60 cc syringes used in Example 1. After processing to form lipid vesicles, the following results were observed:

Sample A (Brij 56 and avocado oil unsaponifiables) had a fluid consistency. Upon microscopic examination, many heterogenous, but small vesicles were visible. After centrifugation at 3500 rpm for 15 minutes, no separation was observed, but a small amount of creaming formed on top of the Sample. Mean particle size of the vesicles, measured by Coulter Counter, was 254 nm.

Sample B (Brij 72 and avocado oil unsaponifiables) had a lotion-like consistency. Upon microscopic examination, many heterogenous vesicles were visible. After centrifugation at 3500 rpm for 15 minutes, no separation was observed. Mean particle size of the vesicles, measured by Coulter Counter, was 765 nm.

Sample C (Brij 76 and avocado oil unsaponifiables) had a fluid consistency. Upon microscopic examination, very nice small vesicles were visible. After centrifugation at 3500 rpm for 15 minutes, 2 ml of hazy solution separated as infernatant. Mean particle size of the vesicles, measured by Coulter Counter, was 281 nm.

Sample D (Brij 97 and avocado oil unsaponifiables) had a very fluid consistency. Upon microscopic examination, both very nice small vesicles and some large vesicles were visible. After centrifugation at 3500 rpm for 15 minutes, no separation was observed, but a small amount of creaming formed on top of the Sample. Mean particle size of the vesicles, measured by Coulter Counter, was 151 nm.

Sample E (Brij 30 and avocado oil unsaponifiables) had a very fluid consistency. Upon microscopic examination, both very nice small vesicles and some large vesicles were visible. After centrifugation at 3500 rpm for 15 minutes, no separation was observed, but a small amount of creaming formed on top of the Sample. Mean particle size of the vesicles, measured by Coulter Counter, was 348 nm.

Sample F (Brij 92 and avocado oil unsaponifiables) had a fluid consistency. Upon microscopic examination, nice spherical vesicles were visible. After centrifugation at 3500 rpm for 15 minutes, 1 ml of turbid aqueous solution separated as infernatant. Mean particle size of the vesicles, measured by Coulter Counter, was 381 nm.

Sample G (Tween 60 and avocado oil unsaponifiables) had a very fluid consistency. Upon microscopic examination, extremely small homogenous vesicles were visible. After centrifugation at 3500 rpm for 15 minutes, no separation was observed, but a small amount of creaming formed on top of the Sample. Mean particle size of the vesicles, measured by Coulter Counter, was 151 nm.

Sample H (Tween 80 and avocado oil unsaponifiables) had the same consistency and size vesicles as Sample G. After centrifugation at 3500 rpm for 15 minutes, no separation was observed. Mean particle size of the vesicles, measured by Coulter Counter, was 164 nm.

Sample I (Myrj 45 and avocado oil unsaponifiables) had a fluid consistency. Upon microscopic examination, very nice looking small vesicles were visible. After centrifugation at 3500 rpm for 15 minutes, no separation was observed, but the Sample took on a lotion-like consistency. Mean particle size of the vesicles, measured by Coulter Counter, was 310 nm.

Sample J (Mona 150 LWA and avocado oil unsaponifiables) had a creamy consistency. Upon microscopic examination, the vesicles appeared similar to those of Sample I (small and nice looking). After centrifugation at 3500 rpm for 15 minutes, no separation was observed. Mean particle size of the vesicles, measured by Coulter Counter, was 252 nm.

Sample K (Mona 150 LWA and avocado oil unsaponifiables) had a fairly thick, creamy consistency. Upon microscopic examination, nicely shaped heterogenous vesicles were visible. After centrifugation at 3500 rpm for 15 minutes, no separation was observed. Mean particle size of the vesicles, measured by Coulter Counter, was 644 nm.

Sample L (Mona 15–70 w and avocado oil unsaponifiables) had the same consistency as Sample K. Upon microscopic examination, the vesicles also appeared similar to those of Sample K, except that they were smaller. After centrifugation at 3500 rpm for 15 minutes, no separation was observed. Mean particle size of the vesicles, measured by Coulter Counter, was 218 nm.

This Example shows that avocado oil unsaponifiables can be used in combination with a variety of primary amphiphiles, in particular the Tween family of ethoxylated sorbitan fatty acid esters, the Brij family of polyoxyethylene fatty ethers, the Myrj family of polyoxyethylene derivatives of stearic acid, and the Mona family of diethanolamides to form good lipid vesicles. None of the samples showed birefringence, probably due to the small particle size of the vesicles.

EXAMPLE 5

In this Example lipid vesicles for use in hair conditioners were formed. The primary amphiphile making up the lipid bilayers consisted of glyceryl distearate in Sample A and polyoxyethylene (8) stearate in Sample B. Stearyl alcohol was added as a secondary amphiphile. The lipid bilayers also contained phytosterol from avocado oil unsaponifiables (supplied by Croda Inc., Parsippany, N.J.). Distearyldimonium chloride was used as a positive charge producing agent.

In the aqueous phase, sodium laurel sulfate (30%) was used as a secondary emulsifier, along with methyldibromo glutaronitrile phenoxyethenol polyquaternium 7 as a preservative. Cetyl trimethyl ammonium chloride was used as a positive charge producing agent.

TABLE 5

(% by weight)

| A | B | |
|---|---|---|
| | | Lipid Phase |
| 1.5 | 0.5 | Stearyl Alcohol |
| 2.0 | | Glyceryl Distearate |
| | 1.7 | Polyoxyethylene (8) Stearate |
| 3.33 | 1.0 | Avocado Oil Unsaponifiables* |
| 2.5 | 2.5 | Distearyldimonium Chloride |
| | | Aqueous Phase |
| 0.5 | 0.5 | Sodium Laurel Sulfate 30% |
| 0.1 | 0.1 | Methyldibromo Glutaronitrile Phenoxyethenol Polyquaternium 7 |
| 0.1 | 2.0 | Cetyl Trimethyl Ammonium Chloride |
| 88.0 | 91.7 | Deionized Water |

*1 gram of Avocado Oil Unsaponifiables contains approximately 0.3 gm of phytosterol The lipid vesicles were hot loaded according to the method described in Example 1. Sample A was processed using a hydration ratio of 1 part lipid at 80° C. to 9.5 parts aqueous at 70° C. Sample B was processed using a hydration ratio of 1 part lipid at 90° C. to 16.5 parts aqueous at 70° C.

After processing to form lipid vesicles, both Samples A and B had a creamy consistency, appropriate for use as a hair conditioner. Upon microscopic examination, the vesicles of both Samples were very good and homogenous.

This Example shows that avocado oil unsaponifiables, which acts both as a structural component of lipid vesicles by supplying phytosterol to the lipid walls, as well as a moisturizing agent by supplying triglycerides to the central cavity can be used along with amphiphiles which also have cosmetic (e.g., moisturizing) properties, such as glyceryl distearate and polyoxyethylene 8 stearate, to form good lipid vesicles suitable for use in cosmetics. Other useful materials (i.e., emulsifiers and preservatives) can also be added to the aqueous portion of the lipid vesicles, such as sodium laurel sulfate (30%) and methyldibromo glutaronitrile phenoxyethenol polyquaternium 7.

EXAMPLE 6

In this Example, lipid vesicles were formed for use in a skin rejuvenating cream. Polyoxyethylene 8 stearate was used as the primary amphiphile and stearyl alcohol, stearyl alcohol-Ceteareth 20 and cetearyl alcohol-Ceteareth 20 were used as the secondary amphiphiles making up the lipid bilayers. Avocado oil unsaponifiables was also added to provide phytosterol to the bilayers and triglycerides to the central cavity. A variety of other moisturizing agents were also added to the lipid phase, such as shark liver oil, petrolatum lanolin-lanolin alcohol, benzoic acid alkyl esters and cetyl acetate-acetylated lanolin alcohol, all of which were encapsulated in the central core of the lipid vesicles. Tocopherol concentrate (vitamin E) and BHA (butylated hydroxy anisol) were added to the lipid phase as antioxidants.

The aqueous portion of the lipid vesicles contained glycerin (99%) and butylene glycol as humectants, sodium DL2 pyrrolidone 5 carboxylate, aloe vera concentrate, SRF (skin respiratory factor) and collagen as moisturizers, di sodium EDTA as a chelating agent, and methyldibromo glutaronitrile phenoxyethenol polyquaternium 7 as an antibacterial agent.

TABLE 6

| % by Weight | |
|---|---|
| | LIPID PHASE |
| 0.5 | Shark Liver Oil |
| 0.1 | Petrolatum-Lanolin-Lanolin Alcohol |
| 0.5 | Benzoic Acid-$C_{12-15}$ Alkyl Esters |
| 0.1 | TOCOPHEROL Concentrate (Vitamin E) |
| 1.5 | Copolyol |
| 3.0 | Stearyl Alcohol - Ceteareth - 20 |
| 0.5 | Stearyl Alcohol |
| 1.0 | Cetearyl Alcohol - Ceteareth - 20 |
| 1.7 | Polyoxyethylene (8) Stearate |
| 1.0 | Avocado Oil Unsaponifiables |
| 0.04 | Fragrance |
| 0.1 | BHA |
| 1.0 | Cetyl Acetate - Acetylated Lanolin Alcohol |
| | AQUEOUS PHASE |
| 4.0 | Glycerin 99% |
| 6.0 | Butylene Glycol |
| 1.0 | Sodium DL2 Pyrrolidone 5 - Carboxylate |
| 0.2 | Aloe Vera Concentrate |
| 0.1 | Di Sodium EDTA |
| 0.1 | Collagen |
| 0.2 | Methyldibromo Glutaronitrile Phenoxyethenol Polyquaternium 7 |
| 0.05 | SRF Powder |
| 7.31 | Deionized Water |

The lipid vesicles were hot loaded according to the method described in Example 1. A hydration ratio of 1 part lipid at 80° C. to 16.5 parts aqueous at 70° C. was used. After processing to form lipid vesicles, the sample had a creamy consistency, appropriate for use as a skin rejuvenating cream. Upon microscopic examination, the vesicles were very good looking and homogenous.

This Example shows that a variety of amphiphiles which have cosmetic properties (i.e., moisturizers) can be used in combination with avocado oil unsaponifiables to form the lipid bilayers and to fill the central cavity of vesicles for use in skin creams. Avocado oil unsaponifiables provides the advantage of acting both as a good structural component of vesicles by providing phytosterol to the lipid bilayers, as well as a moisturizing agent by providing triglycerides to the central cavity.

EXAMPLE 7

In this Example, lactic acid carrying lipid vesicles were formed for use in dermatologicals. The lipid bilayers of the vesicles were made up of glycerol distearate as the primary amphiphile, polyoxyethylene 10 stearyl ether, stearyl alcohol-Ceteareth 20, cetearyl alcohol-Ceteareth 20 and stearyl alcohol as secondary amphiphiles, and phytosterol supplied by avocado oil unsaponifiables. Other materials included in the lipid phase to be encapsulated in the central core of the vesicles were lactic acid (88%) (a dead skin cell remover), and cetyl acetate-acetylated lanolin alcohol, alkyl lactate and octyl hydroxystearate (skin moisturizers).

The aqueous phase included methyl paraben as a preservative, Bronopol (methyldibromo glutaronitrile phenoxyethenol polyquaternium 7) and propyl paraben as antibacterials, glycerin (96%) as a humectant, and Polysorbate 80 (polyoxyethylene 20 sorbitan monooleate) as a secondary emulsifier.

TABLE 7

| % by Weight | |
|---|---|
| | LIPID PHASE |
| 5.7 | Lactic Acid 88% |
| 1.4 | Polyoxyethylene 10 Stearyl Ether |
| 3.3 | Avocado Oil Unsaponifiables |
| 6.3 | Octyl Hydroxystearate |
| 2.8 | Glycerol Distearate |
| 3.0 | Stearyl Alcohol - Ceteareth 20 |
| 1.0 | Cetearyl Alcohol - Ceteareth 20 |
| 1.0 | Stearyl Alcohol |
| 1.0 | Cetyl Acetate and Acetylated Lanolin Alcohol |
| 1.5 | C 12–15 Alkyl Lactate |
| | AQUEOUS PHASE |
| 0.2 | Methyl Paraben |
| 4.0 | Glycerin 96% |
| 1.24 | Sodium Hydroxide |
| 0.03 | Propyl Paraben |
| 0.10 | Sodium Chloride |
| 0.75 | Polysorbate 80 |
| 0.05 | Bronopol |
| 4.0 | Silicone Emulsion |
| 0.2 | Fragrance |
| 62.93 | Deionized Water |

The lipid vesicles were hot loaded according to the method described in Example 1. A hydration ratio of 1 part lipid at 70° C. to 16.5 parts aqueous at 60° C. was used. After processing, the sample had a creamy consistency, appropriate for use in dermatological preparations. Upon microscopic examination, the vesicles were very good looking and homogenous.

This Example shows that avocado oil unsaponifiables can be used with amphiphiles and other materials having dermatological properties to form lipid vesicles for use in dermatologicals. Avocado oil unsaponifiables provides the advantage of acting both as a source of phytosterol for the lipid bilayers, as well as a source of triglycerides (moisturizing agent) to be encapsulated in the central cavity of the vesicles.

The foregoing Examples are merely illustrative and those skilled in the art may be able to determine other materials and methods which accomplish the same results. Such other materials and methods are included within the following claims.

What is claimed is:

1. A paucilamellar lipid vesicle having 2–10 bilayers surrounding an amorphous oil-filled central cavity, wherein each of said bilayers contains at least one non-phospholipid amphiphile selected from the group consisting of polyoxyethylene fatty esters, polyoxyethylene fatty acid ethers, diethanolamides, long chain acyl hexosamides, long chain acyl amino acid amides, long chain acyl amides, POE (20) sorbitan mono- or trioletate, and glycerol monostearate as the primary lipid in said bilayers and phytosterol supplied by avocado oil unsaponifiables, said avocado oil unsaponifiables partitioning in manufacture of said paucilamellar lipid vesicles, so that a sufficient amount of the phytosterol from said avocado oil unsaponifiables goes into said bilayers so as to stabilize said bilayers and the remainder of said avocado oil unsaponifiables goes into said amorphous central cavity.

2. The paucilamellar vesicle of claim 1, wherein said polyoxyethylene fatty esters have the formula $$R_1-COO(C_2H_4O)_nH$$

where $R_1$ is lauric, myristic, cetyl, stearic, or oleic acid, and n32 2–10;

said polyoxyethylene fatty acid ethers have the formula $$R_2-CO(C_2H_4)_nH$$

where $R_2$ is lauric, myristic or cetyl acids, single or double unsaturated octadecyl acids, or double unsaturated eicodienoic acids and m ranges from 2–4;

said diethanolamides have the formula $$(HOCH_2-CH_2)_2NCO-R_3$$

where R3 is caprylic, lauric, myristic, or linoleic acids;

said long chain acyl hexosamides have the formula $$R_4-NHCO-(CH_2)_b-CH_3$$

where b ranges from 10–18 and $R_4$ is a sugar molecule selected from a group consisting of glucosamine, galactosamine, and N-methylglucamine;

said long chain acyl amino acid amides have the formula $$R_5-CH(COOH)-NHCO-(CH_2)_c-CH_3$$

where c ranges from 10–18 and $R_5$ is an amino acid side chain;

said long chain acyl amides have the formula $$HOOC-(CH_2)_d-N(CH_3)-(CH_2)_3-NCHO-R_6$$

where $R_6$ is an acyl chain having 10–20 carbons and not more than two unsaturations, and d ranges from 1–3.

3. The paucilamellar vesicle of claim 2, wherein said bilayers further comprise a second material selected from the group consisting of phospholipids, glycolipids, and mixtures thereof.

4. The paucilamellar lipid vesicle of claim 1, wherein said primary non-phospholipid amphiphile is selected from the group consisting of betaines and anionic sarcosinamides.

5. The paucilamellar lipid vesicle of claim 1, wherein said primary non-phospholipid amphiphile is selected from the group consisting of $C_{12}-C_{18}$ fatty alcohols, $C_{12}-C_{18}$ glycol monoesters, $C_{12}-C_{18}$ glyceryl mono- and diesters, propylene glycol stearate, sucrose distearate, and mixtures thereof; and wherein said bilayers further comprise a second non-phospholipid amphiphile selected from the group consisting of quaternary dimethyldiacyl amines, polyoxyethylene acyl alcohols, polyglycerols, sorbitan fatty acid esters, polyoxyethylene derivatives of sorbitan fatty acid esters, fatty acids and their salts, and mixtures thereof.

6. The paucilamellar lipid vesicle of claim 5, wherein said primary non-phospholipid amphiphile is selected from the group consisting of C16–C18 fatty alcohols, glycol stearate, glyceryl mono- and distearate, glyceryl dilaurate, and mixtures thereof.

7. The paucilamellar lipid vesicle of claim 5 wherein said second non-phospholipid amphiphile is selected from the group consisting of stearyl alcohol, polyoxyethylene fatty alcohols, polyoxyethylene derivatives of sorbitan fatty acid esters having 10–20 oxyethylene groups, and mixtures thereof; wherein the fatty alcohol or fatty acid groups of the polyoxyethylene fatty alcohols and the polyoxyethylene derivatives of sorbitan fatty acid esters are selected from the group consisting of radicals of palmitic acid, stearic acid, lauric acid, and oleic acid, and mixtures thereof.

* * * * *